(12) United States Patent
Shepard

(10) Patent No.: US 7,537,444 B2
(45) Date of Patent: May 26, 2009

(54) METHOD AND APPARATUS FOR PRODUCING A SOLID PRODUCT FOR DENTAL USAGE

(76) Inventor: John S. Shepard, 2550 S. Stover, Fort Collins, CO (US) 80525

( * ) Notice: Subject to any disclaimer, the term of this patent is extended or adjusted under 35 U.S.C. 154(b) by 733 days.

(21) Appl. No.: 10/908,529

(22) Filed: May 16, 2005

(65) Prior Publication Data

US 2006/0255039 A1    Nov. 16, 2006

(51) Int. Cl.
*A61C 13/14* (2006.01)
(52) U.S. Cl. .............. 425/387.1; 425/405.1; 425/405.2; 425/445; 219/440; 219/431
(58) Field of Classification Search .............. 425/405.1, 425/405.2, 445; 220/281, 266; 219/440, 219/431
See application file for complete search history.

(56) References Cited

U.S. PATENT DOCUMENTS

| 3,632,014 | A | * | 1/1972 | Basile .................... 220/203.29 |
| 4,771,162 | A | * | 9/1988 | Schatz et al. ................. 219/400 |
| 4,796,776 | A | * | 1/1989 | Dalquist et al. ......... 220/203.05 |
| 5,444,218 | A | * | 8/1995 | Zelniker et al. ............. 219/440 |

* cited by examiner

*Primary Examiner*—Philip C Tucker
*Assistant Examiner*—Xue Liu
(74) *Attorney, Agent, or Firm*—Ancel W. Lewis, Jr.

(57) ABSTRACT

An apparatus and method for producing a solid product such as orthopedic appliances, dental splint mouthpieces, dentures, lined dentures and the like from flowable materials such as silicones, acrylics, polyurethanes and dental casting investments. The container in which an article is treated will develop 80-100 psi and has opposed curved surfaces between which a seal is formed without leakage.

10 Claims, 3 Drawing Sheets

METHOD AND APPARATUS FOR PRODUCING A SOLID PRODUCT FOR DENTAL USAGE

TECHNICAL FIELD

This invention relates to product production and more particularly a method and apparatus for producing a solid product that is particularly suitable for dental appliance usage.

BACKGROUND ART

There are a number of dental applications including orthopedic appliances, dental splints, mouthpieces, dentures, and lined dentures that utilize a flowable material that is changed to a solid product. Typical flowable materials are silicones, acrylics, polyurethanes and dental casting investments.

For making a denture a dental acrylic begins as a two-part liquid and powder (flowable material) and then is changed to a solid denture product. Undesirable air bubbles usually of microscopic size form in the solid product when done at atmospheric pressure or at pressures below 50 psi. A further example of the use of two of the above flowable materials are the acrylic denture to which is applied a liner of silicone. A good bond between the denture and liner without the formation of air bubbles in or between the materials is desirable.

Prior known pressurized containers heretofore provided for similar purposes use pressures of about 20 psi to 35 psi. These containers were not effective for some materials particularly silicones because micro-bubbles tend to form in the solid product. Another deficiency in the prior art containers is that a seal was formed between opposed flat surfaces and these tend to leak when pressures increase to above 50 psi.

SUMMARY OF THE INVENTION

A method and apparatus has a body of flowable material with air bubbles that is pressurized at a higher pressure and during a selected time interval to drive out the air bubbles as the material changes from a flowable state to a solid state. The time interval varies according to the material and may range from about 20 minutes to 13 hours. The apparatus disclosed includes a container preferably of elliptical shape having a domical top wall with an opening and a lid inside the container with the curvature of the top wall and the lid complementary so that a flexible seal between the two curved surfaces causes an effective sealing under pressure. The container is pressurized to a pressure above 50 psi and preferably to a pressure between about 80 psi and 100 psi to drive out air bubbles from the material as the material changes from a flowable state to a solid state. The flowable materials are silicones, acrylics, polyurethanes and dental casting investments.

BRIEF DESCRIPTION OF THE DRAWINGS

Details of this invention are described in connection with the accompanying drawings that bear similar reference numerals in which.

DETAILED DESCRIPTION OF THE INVENTION

Figure 1:
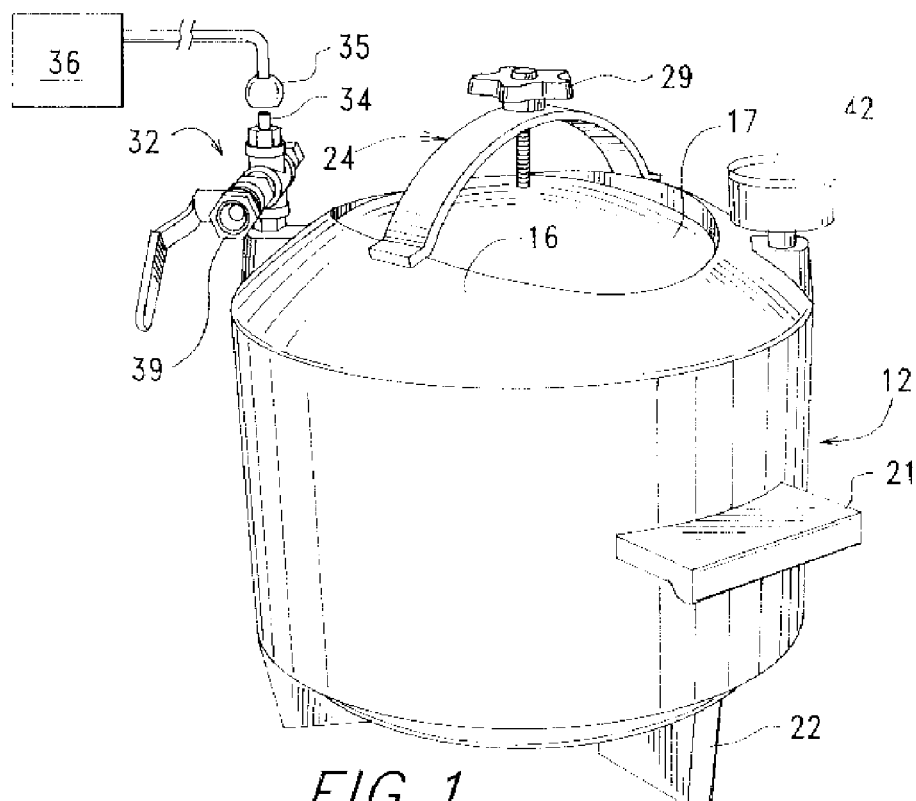
FIG. 1 is a top perspective view of a pressurizing container embodying features of the present invention.
Figure 2:
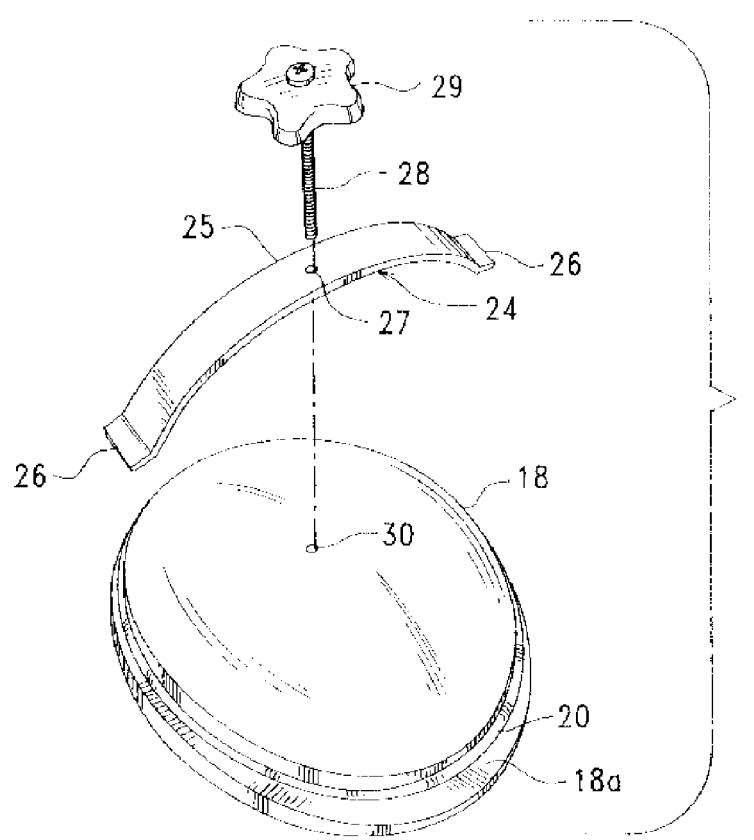
FIG. 2 is an exploded view of a portion of the lid and clamp for the lid.
Figure 3:
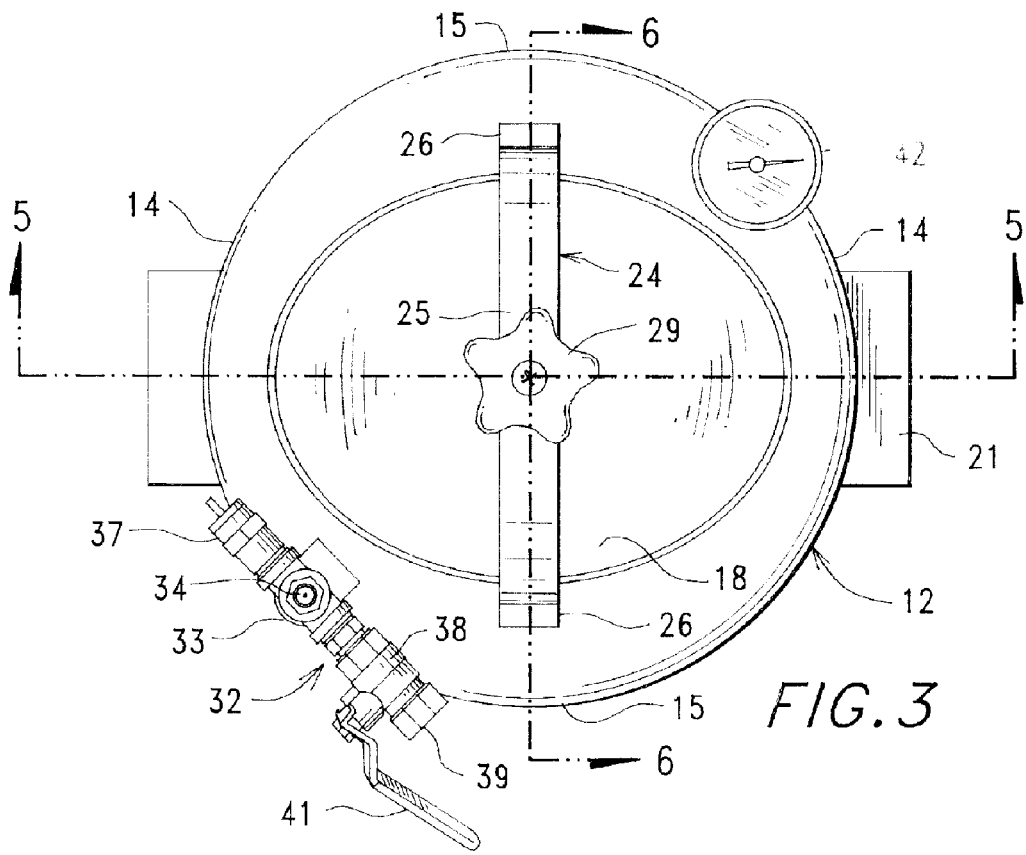
FIG. 3 is a top plan view of FIG. 1 with the lid in a closed position.
Figure 4:
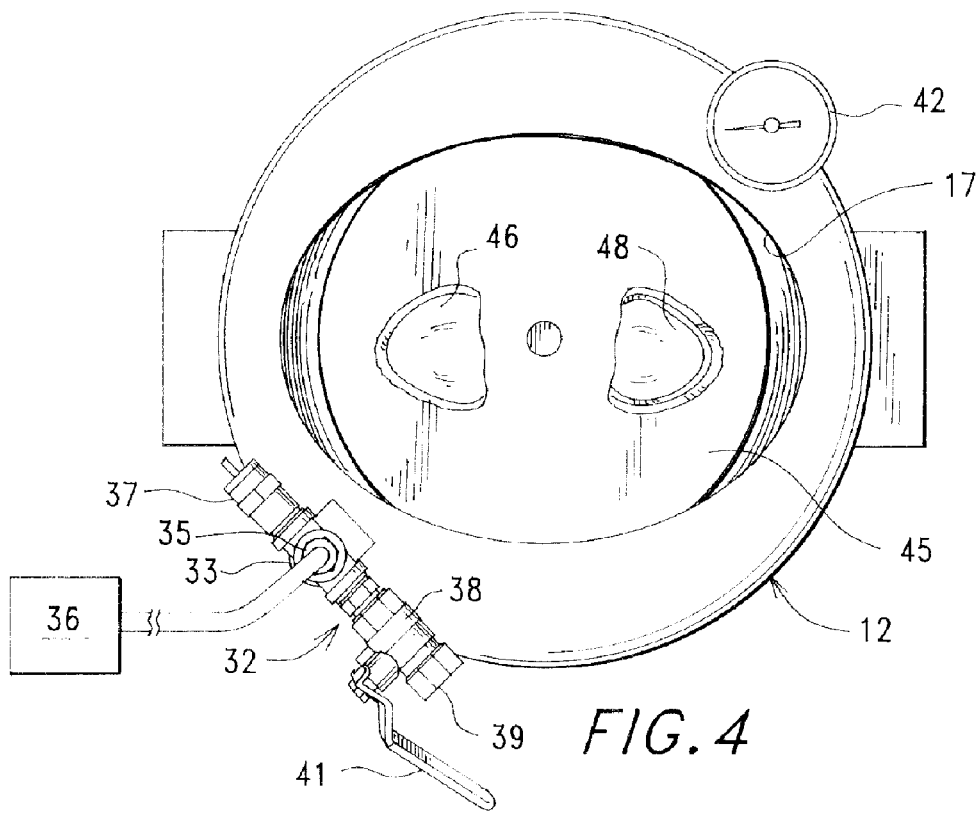
FIG. 4 is a top plan view of the container without the lid.
Figure 5:
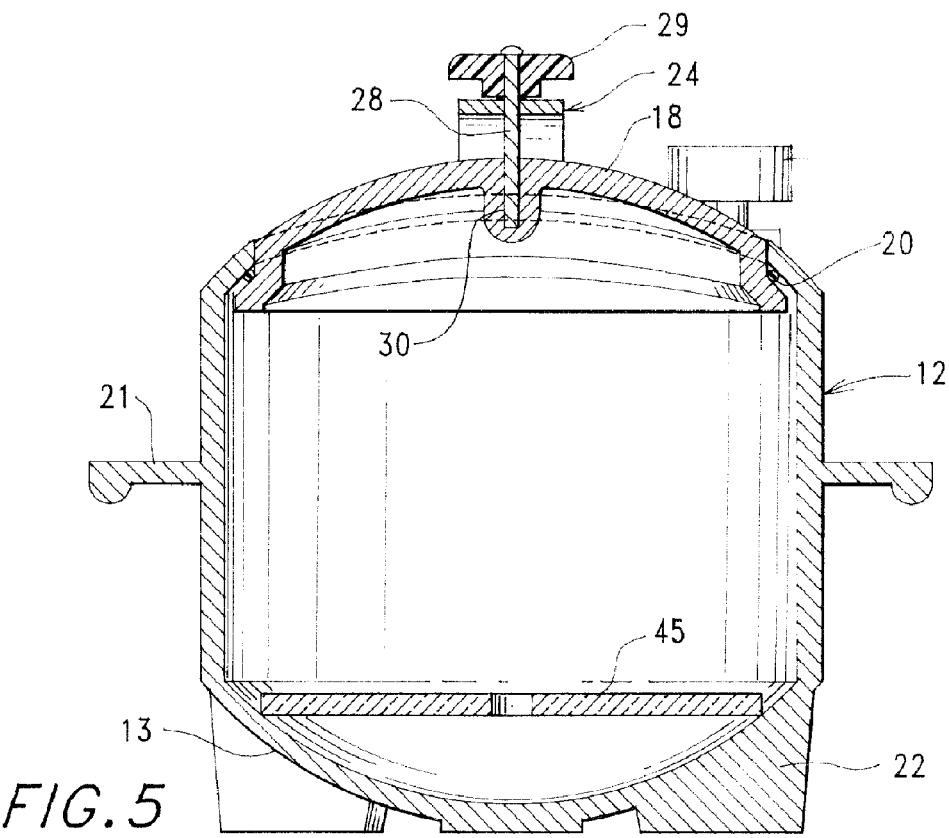
FIG. 5 is a sectional view taken along line 5-5 of FIG. 3.
Figure 6:
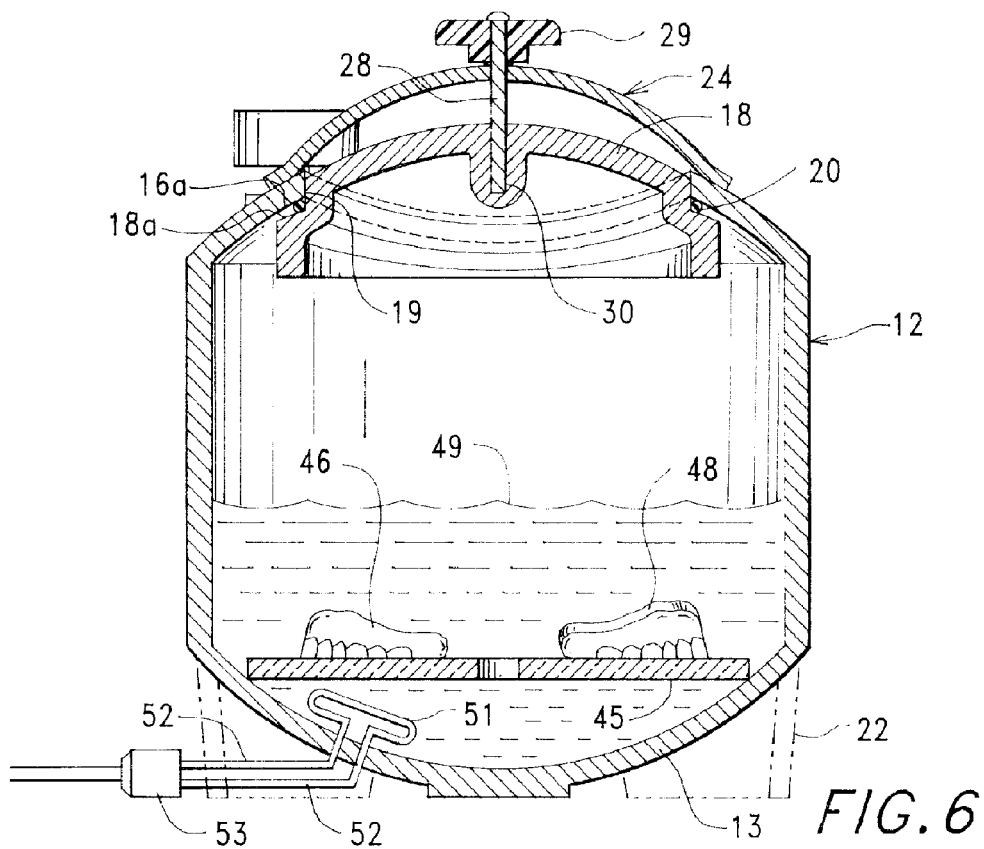
FIG. 6 is a sectional view taken along line 6-6 of FIG. 3.

Referring now to FIGS. 1-6 there is shown a pressurizing container 12 embodying features of the present invention having a dished bottom wall 13, a pair of opposed, spaced, curved end wall portions 14 and a pair of opposed, spaced, curved side wall portions 15 arranged in an elliptical shape and extending up from the bottom wall 13, a domical top wall 16 extending in and up from the top of wall portions 14 and 15 and provided with an elliptical top opening 17. A curved lid 18 of elliptical shape is provided inside the container that is removable from the container. The lid 18 has a step or notch 19 inwardly of the outer peripheral edge providing a domical curved top surface 18a that is opposite and complementary in shape with the curved undersurface 16a of the top wall 16. A ring shaped or endless flexible seal 20 flexes to fit in the notch 19 and rests on the top surface 18a of lid 18.

A lid clamping assembly includes a clamping bracket 24 with a bow shaped main body 25 and flared end portions 26, a through hole 27 centered in the top, an externally threaded bolt 28 in and spaced from the main body to be slidable therein with a turning knob 29 affixed to the top end of bolt 28. The lid 18 has an internally threaded center hole 30 into which the bolt 28 is threaded. The bracket 24 straddles the lid 18 with end portions 26 resting on the top wall outside the center opening 17. Once the articles to be treated are place in the container the knob is turned to draw the lid up and compress the seal 20 between surfaces 16a and 18a. A threading in the opposite direction will release the lid for removal. The elliptical shape of the hole 17 and lid 18 allows the lid to be readily removed from and put back inside the container 12. The seal 20 is further compressed between the lid top surface 18a and container undersurface 16a when the container is pressurized.

A pair of opposed handles 21 extend out from opposite sides of the end wall portions. Three feet 22 are mounted at circumferentially spaced intervals of 120 degrees extend down than the outside of the bottom wall 13 to support the container 12 upright. The container and lid are preferably formed from cast aluminum.

An air control valve 32 is mounted to the container 12 which includes a housing 33 attached to the top wall 16 in flow communication with the inside of the container, an air input valve coupling 34 extending up from the housing to releasable couple with a female coupling head 35 connected for an air source 36 such as a compressor. A pressure relief valve 37 is at one end of the housing 33 and a manual on-off valve 38 is connected at the opposite end with an air discharge outlet 39 with a control lever 41 to enable air to flow through the valve and to the atmosphere to depressurize the container. A pressure gauge 42 is mounted on the top wall 16 opposite the air valve to indicate the pressure inside the container.

A flat support plate 45 is shown resting on the bottom wall 13 to provide a horizontal surface for the articles to be pressurized. The articles to be pressurized according to the present invention are shown disposed on plate 45 as an acrylic and denture 46 as well as a similar denture with a lining 48 of silicone. The container is shown as containing a quantity of water 49 in which the plate 45 and treated articles 46 and 48 are submerged. The water in the container serves to equalize the pressure around the article being treated. For heating purposes, if desired, there is provided a heating device 51 shown as an electric coil in the bottom of the container below plate 45 having a pair of electric lines 52 and an electric plug 53 connected to electric power input lines shown as a means to heat the container and the contents therein for some applications.

The time interval for the treatment will vary according to the material being treated. Typical time intervals for acrylics is about 20 minutes to 30 minutes for silicones about 12 hours to 13 hours for polyurethanes about 6 hours to 8 hours and for dental casting investments about 30 minutes to 60 minutes.

In a full sequence of operation the product to be treated is placed in the container on the support plate 45 and water is added, the clamp assembly is tightened so that the seal 20 is slightly compressed between the lid and container. The control valve 32 is operated to pressurize the container to a select pressure. Heat is applied, if desirable, and at the end of the selected time interval the container is depressurized by activating the lever 41. The handle 29 is turned to open the lid so the product treated may be removed.

Although the present invention has been described with a certain degree of particularity, it is understood that the present disclosure has been made by way of example and that changes in details of structure may be made without departing from the spirit thereof.

What is claimed is:

1. Apparatus for producing a solid product without air bubbles comprising:

a pressurizing container have a top wall with a curved undersurface and a top opening, a lid inside said container for closing and sealing said top opening, said lid having a curved top surface extending inwardly from an outer peripheral edge to a notch, said top surface being opposite and complementary with said curved undersurface, said notch extending up from transverse to said top surface said notch being sized and shaped to fit into and extend through said top opening to center said lid in said top opening, a flexible seal supported by said top surface and said notch, said notch locating said seal relative to said top opening around the entire periphery of said top opening and between said curved undersurface and top surface that is compressed between said top surface and said undersurface and restrained along one side of said seal by said notch when said container is pressurized for sealing said top opening closed, a body of flowable materials with air bubbles in said container, and means for pressurizing said container to a pressure above 50 psi for a selected time interval sufficient to force said top surface toward said undersurface to compress said seal and to drive out said air bubbles from said material as said material is changed from a flowable state to a solid state.

2. The apparatus as set forth in claim 1 wherein said container has a dished bottom wall, a pair of opposed, spaced, curved end wall portions, a pair of opposed, curved, spaced side wall portions arranged in an elliptical shape, said top wall being domical and extending in and up from said end and side wall portions, and said top opening being elliptical.

3. The apparatus as set forth in claim 2 wherein said lid is of an elliptical shape, providing a domical curved top surface that is opposite and complementary in shape with said curved undersurface of said top wall, said seal being disposed between said undersurface and said top surface.

4. The apparatus as set forth in claim 1 including a control valve assembly for controlling air flow into and out of said container to pressurize said container.

5. The apparatus as set forth in claim 4 wherein said control valve assembly includes a housing attached to said top wall and in flow communication with the inside of said container, an air input valve coupling extending from said housing for coupling an air source to said control valve, a pressure relief valve at one end of said housing and an on-off valve at an opposite end of said housing to depressurize said container.

6. The apparatus as set forth in claim 4 including a pressure gauge on said container to indicate the amount of pressure in said container.

7. The apparatus as set forth in claim 1 including a lid clamping assembly having a clamping bracket with a bow shaped main body and flared end portions that rest on said top wall outside said top opening, a through hole in said main body, a threaded bolt slidable in said through hole, and a turning knob affixed to a top end of said bolt, said bolt threading into said lid to draw said lid upwardly toward said top wall.

8. The apparatus as set forth in claim 1 wherein said lid and top opening are of an elliptical shape to allow said lid to be placed in and removed from inside said container.

9. The apparatus as set forth in claim 1 wherein said body flowable material includes silicones, acrylics, polyurethanes and dental instruments.

10. Apparatus for producing a solid product without air bubbles comprising:

a pressurizing container having a bottom wall, opposed end walls and opposed side walls and a domical top wall with a curved undersurface and an elliptical top opening, a lid inside said container for closing said top opening having a curved top surface extending inwardly from an outer peripheral edge to a notch, said top surface being opposite and complementary with said undersurface, said notch extending up from and extending transverse to said top surface, said notch sized and shaped to fit into and extending through said top opening, said lid being removable from said container via said top opening, a flexible seal supported by said top surface and said notch, said notch locating from movement by said seal relative to said top opening around the periphery of said top opening and between said curved undersurface and said top surface that is compressed between said top surface and said undersurface and restrained along one side of said seal by said seal when said container is pressurized for sealing said top opening closed, a clamp assembly for drawing said lid upwardly toward said top wall, a body of flowable material with air bubbles in said container, and means for pressurizing said container to a selected pressure to 80 psi to 100 psi for a selected time interval sufficient to force said top surface toward said undersurface to compress said seal and to drive out said air bubbles from said material as said material is changed from a flowable state to a solid state.

* * * * *